(12) United States Patent
Holt

(10) Patent No.: US 7,517,850 B2
(45) Date of Patent: Apr. 14, 2009

(54) CALCIUM PHOSPHATE NANOCLUSTERS AND THEIR APPLICATIONS

(76) Inventor: Carl Holt, c/o Hannah Research Institute., Ayr. Ayrshire KA6 5HL. (GB)

( * ) Notice: Subject to any disclaimer, the term of this patent is extended or adjusted under 35 U.S.C. 154(b) by 0 days.

(21) Appl. No.: 11/450,879

(22) Filed: Jun. 12, 2006

(65) Prior Publication Data

US 2006/0293220 A1 Dec. 28, 2006

Related U.S. Application Data

(62) Division of application No. 10/149,206, filed as application No. PCT/GB00/04827 on Dec. 15, 2000, now Pat. No. 7,060,472.

(30) Foreign Application Priority Data

Dec. 17, 1999 (GB) ................................. 9929919.0

(51) Int. Cl.
- *A61K 38/16* (2006.01)
- *A61C 5/00* (2006.01)
- *A61C 5/04* (2006.01)

(52) U.S. Cl. ......................... 514/7; 433/217.1; 433/226

(58) Field of Classification Search .................. None
See application file for complete search history.

(56) References Cited

U.S. PATENT DOCUMENTS

| | | |
|---|---|---|
| 5,015,628 A | 5/1991 | Reynolds |
| 5,227,154 A | 7/1993 | Reynolds |
| 5,508,267 A | 4/1996 | Czernuszka et al. |

2003/0049808 A1 3/2003 Holt

FOREIGN PATENT DOCUMENTS

| | | |
|---|---|---|
| WO | WO 93/07910 | 4/1993 |
| WO | WO 98/40406 | 9/1998 |

OTHER PUBLICATIONS

Sood et al. Monomer Characterization and Studies of Self-Association of the Major B-Casein of Human Milk. J Dairy Sci. 1997, vol. 80, pp. 1554-1560.*

Speer et al. Regulation of cardiovascular calcification. Cardiovascular Pathology.Mar.-Apr. 2004. vol. 13, Issue 2, pp. 63-70.*

Database Chemabs 'Online! Chemical Abstract Service, Columbus, Ohio; Carl Holt et al.; "A coreshell model of calcium phosphate nanoclusters stabilized by beta-caein phosphopeptides, derived from sedimentation equilibrium and small-angle x-ray and neutron-scattering measurements;" Database Accession No. 128:254299 CA.

Database Chemabs 'Online! Chemical Abstract Service, Columbus, Ohio; Carl Holt et al.; Ability of a beta-casein phosphopeptide to modulate the precipitation of calcium phosphate by forming amorphous dicalcium phosphate nanoclusters; Database Accession No. 124:253788 CA.

Reynolds: Remineralization of Enamel Subsurface Lesions by Casein Phosphopeptide-stabilized Calcium Phosphate Solutions. J Dent Res. Sep. 1997. vol. 76, No. 9: pp. 1587-1595.

Nakano et al.: Preparation and characterization of milk calcium salts by using casein phosphopeptide. Prep Biochem Biotechnol. May 2000, vol. 30, No. 2, pp. 155-166.

* cited by examiner

*Primary Examiner*—Marcela M Cordero Garcia
(74) *Attorney, Agent, or Firm*—Nixon & Vanderhye, P.C.

(57) ABSTRACT

Artificial particles known as calcium phosphate nanoclusters are disclosed. The particles contain high concentrations of calcium, particularly for use in nutritional products, neutraceuticals, and pharmacological preparations.

21 Claims, 1 Drawing Sheet

CALCIUM PHOSPHATE NANOCLUSTERS AND THEIR APPLICATIONS

Figure 1:
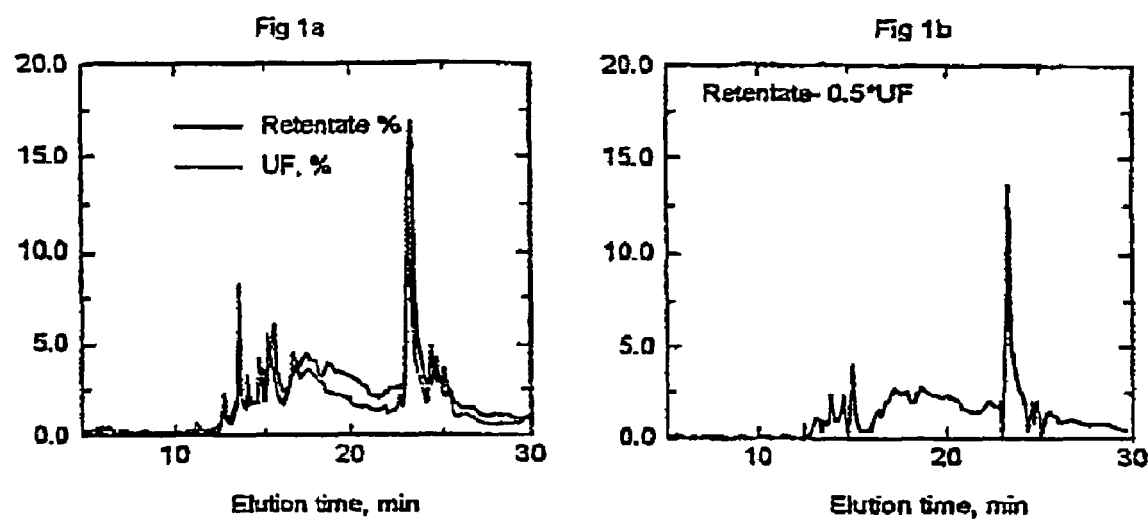

This application is a divisional of U.S. application Ser. No. 10/149,206, which was filed on Sep. 4, 2002, and which has now issued as U.S. Pat. No. 7,060,472. Application Ser. No. 10/149,206 was itself a U.S. National Stage of International Application No. PCT/GB2000/04827, which was filed on Dec. 15, 2000, and which claims priority to the filing date of United Kingdom Application No. 9929919.0 which was filed on Dec. 17, 1999. The contents of all of the above-identified applications are hereby incorporated by reference.

The present invention relates to the field of calcium phosphate nanoclusters and their applications in high calcium content nutritional products, nutraceuticals and pharmacological preparations for use in treatment of pathological calcification.

It is important for mammals to have a high intake of dietary calcium. When this is not achieved in humans, bone diseases such as rickets or osteoporosis may result. There is a market for high calcium content nutritional and nutraceutical preparations; for example, calcium tablets for prevention of osteoporosis and sports/nutraceutical calcium containing drinks. Clearly, milk contains a high concentration of calcium and many of these drinks deliberately aim to provide calcium without the fat etc. associated with milk. Many of these drinks contain calcium gluconate, being a salt of calcium with a reasonably high solubility, allowing the drink to have the same calcium content as milk but with a lower phosphate concentration. However, these are limited in their maximum calcium concentration and also have a sweet taste (and some calorie content) due to the gluconate which is not always appropriate to the application.

It is a first aim of the present invention to provide a method for achieving drinks, solid foods, supplements and the like containing a higher concentration of calcium than is possible with calcium gluconate. The higher the concentration that can be achieved, the lower the volume that must be drunk to enable a consumer to gain their recommended daily amount of calcium. A linked aim is to provide stable materials that can be easily stored, preferably for long period of time. A further linked aim is to provide heat-sterilizable high calcium materials.

A further linked aim is to provide a soluble formulation of essential trace elements in a high calcium solution as an aid to the absorption of otherwise insoluble micronutrients.

In the body, there are pathologies associated with the precipitation of calcium. For example, pathological calcification in the mammary gland is a problematic disease in which milk stones (*corpora amylacea*) form. An additional major aim of the present invention is to provide a preparation for the treatment of pathological calcification. This might be achieved by binding the nanoclusters to a suitable ion-permeable matrix, for example gelatin gel. A gel of caseins might also be used. This would have the advantage of not having other potentially allergenic material in its structure.

Calcium phosphate nanoclusters would also be applicable to dental care products such as mouth washes and toothpastes. Exposure of teeth to calcium phosphate nanoclusters will inhibit or prevent the demineralisation of teeth and application of a phosphopeptide containing gel or other suitable solid containing phase to the teeth could inhibit calcification of dental plaque or even reverse it. A further application would be in the prevention of calcification of medical prostheses such as urinary catheters and heart valves since pathological calcification is a major reason for the failure of these devices. In this method for preventing pathological calcification there would be formed on the surface an equilibrium nanocluster like structure, which can be reversed at will, rather than irreversible precipitation of a calcium salt.

In mammals, nature has already addressed the problems of calcium concentration in the form of milk. Milk contains a high concentration of calcium and phosphate as a foodstuff for growing young. Mammalian milk has been found to contain casein micelles which contain calcium, phosphate and casein. It has been hypothesized that a function of these micelles is to allow milk to have a high calcium and phosphate concentration without causing pathological calcification in normal conditions.

In recent years, artificial particles containing high concentrations of calcium and phosphate have been disclosed. [Carl HOLT et al., Biochem J., 314, 1035-1039 (1996); Carl HOLT et al., Eur. J. Biochem, 252, 73-78 (1998); Carl HOLT et al., Advanced Dairy Chemistry, Vol. 3: Lactose, Water, Salts and Vitamins (P. F. Fox, Ed.)] These are known as Calcium Phosphate nanoclusters.

Calcium phosphate nanoclusters have been made from complex salt mixtures; for example, 37 mM $Ca(NO_3)$, 6 mM $Mg(NO_3)_2$, 36 mM $KNO_3$, 25 mM $KH_2PO_4$, 5 mM $K_2HPO_4$, 1.54 mM $NaN_3$ (as a preservative) [Holt et al., 1998]

or 30 mM $Ca(NO_3)$, 4 mM $Mg(NO_3)_2$, 30 mM tripotassium citrate, 20 mM $KH_2PO_4$, 26 mM $KNO_3$, 1.5 mM $NaN_3$ (as a preservative) [Holt et al., 1996]

These solutions also contained a pure single phosphopeptide, β-casein 4P(f1-25) [Holt et al., 1996], or β-casein 5P(f1-42) [Holt et al., 1998].

Both of these solutions were initially at pH5.5. The pH has to be raised to form calcium phosphate nanoclusters. A problem perceived in these papers was that if the salt solutions were mixed crudely with e.g. a higher pH solution, there would be crude precipitation of calcium phosphate, spoiling the formation of nanoclusters. Furthermore, variation throughout two solutions being mixed would lead to nonuniform nanoclusters, reducing their homogeneity. This problem was solved in these papers by generating ammonia homogeneously in solution from the breakdown of urea by jack bean urease.

At the present date, the publicly understood theory of nanocluster formation is that calcium phosphate precipitates from a supersaturated solution but does so by first forming nuclei that grow to form the macroscopic phase. The action of the phosphopeptide is perceived to be one in which it coats the nuclei in a protective layer which slows down their growth into the precipitate (kinetic stabilization theory). This theory is clearly stated in the latest published work [Holt, C., Timmins, P. A., Errington, N. & Leaver, J. (1998). A core-shell model of calcium phosphate nanoclusters derived from sedimentation equilibrium and small angle X-ray and neutron scattering measurements European Journal of Biochemistry 252, 73-78] is extensively described in a review article [(Holt, C. (1997) The milk salts and their interaction with casein. In: Advanced Dairy Chemistry, Vol. 3: Lactose, Water, Salts and Vitamins (P. F. Fox, Ed.), Chapman and Hall, London, pp. 233-254)]. Thus, nanoclusters are seen as intrinsically unstable particles that would, given enough time, themselves precipitate. Hence, magnesium and citrate, which are known to be inhibitors of the rate of precipitation are thought to help the more powerful phosphopeptide to form stable intermediate nanoclusters and so are considered essential. Magnesium and citrate present in solution were found to be incorporated into the resulting nanoclusters (Holt et al. 1996). The urea/urease method has been used to raise the pH as the gentlest possible method of doing so.

According to the kinetic stabilization theory, simple mixing together of strong base with an acidic solution of calcium, phosphate and phosphopeptide would give rise to a product which depended on the exact conditions of stirring and the transient concentration gradients of mixing and which would therefore be difficult to reproduce or do rapidly. Moreover, in the presence of even tiny amounts of the thermodynamically more stable precipitated phase, the precipitate would grow at the expense of the nanoclusters.

Lastly, currently accepted theory suggests that a mixture of phosphopeptides, such as the ones obtained from whole casein would be ineffective since some of the phosphopeptides would be capable of bridging between two nanocluster particles to create a network or gel while others contained fewer than the requisite number of phosphorylated residues. Thus it is thought that nanocluster formation would only occur under carefully controlled conditions which eliminated concentration and pH gradients. Hence the urea/urease method is considered essential to forming stable nanocluster solutions and it is also considered imperative to use a pure phosphopeptide.

There is described herein developments which show that this generally accepted model is incorrect. As a result, a simpler and substantially more commercially viable method of preparing calcium phosphate nanoclusters has been developed and is described herein. Furthermore, nanoclusters of a new composition are also disclosed.

In this document, a centre of phosphorylation is a region of a peptide o protein containing 3 or more phosphorylated residues in a short sequence.

According to a first aspect of the present invention there is provided a method of making calcium phosphate nanoclusters comprising the preparation of a nanocluster forming solution, a nanocluster forming solution containing appropriate concentrations of calcium ions, phosphate ions and multiply phosphorylated phosphopeptide molecules and having an appropriate pH for formation of calcium phosphate nanoclusters, the method being characterized in that the calcium phosphate nanocluster forming solution is made by mixing together two solutions neither of which is itself a nanocluster forming solution but which contain components such that, when they are combined, they form a calcium phosphate nanocluster forming solution.

Preferably, a phosphopeptide molecule has a centre of phosphorylation.

Preferably, a centre of phosphorylation has at least 3 phosphorylated residues.

More preferably, a centre of phosphorylation has at least 3 phosphorylated residues close together in the multiply phosphorylated peptide.

Most preferably, a centre of phosphorylation has at least 3 phosphorylated residues in a series of 6 consecutive residues in the primary structure of the phosphopeptide molecule.

Preferably, a phosphopeptide molecule contains few or no hydrophobic regions.

Preferably also, a phosphopeptide molecule contains only one centre of phosphorylation.

A nanocluster may have a plurality of different types of phosphopeptide molecule.

Typically, the phosphopeptide molecules will be a mixture.

The mixture of phosphopeptide molecules may be an enzymatic digest of a crude casein preparation.

Typically, the thermodynamic activities of calcium and phosphate ions in solution formed from the two solutions combined are large enough to exceed a solubility-product type relationship such as that found in milk:

$$K_s = \{Ca^{2+}\}\{PO_4^{3-}\}^{0.2}\{HPO_4^{2-}\}^{0.7};$$
$$1.6.10^{-7} \leq K_s \leq 10^{-6} M^{1.9}.$$

Where the curly brackets denote activity.

Most preferably, the nanocluster forming solution has $[Ca_t]/[PP] \leq 3$; $[P_{i,t}] = (0.875 \pm 0.125)$, $[PP] = 1.67 \pm 0.25$; where [PP] is the concentration of the phosphopeptide in grams per litre, $[P_{i,t}]$ is the total millimolar concentration of inorganic phosphate and $[Ca_t]$ is the total millimolar calcium concentration.

Preferably also, the nanocluster forming solution does now contain significant amounts (greater than 0.1 mM) of other calcium chelating agents.

Preferably, if a calcium chelating agent such as nitrate is included there must be an increased amount of calcium allowed in the formulation.

The nanocluster forming solution may contain no magnesium.

A dispersing agent may be added.

A preservative may also be added.

The resulting nanocluster solution may be sterilized.

The resulting nanocluster solution may be freeze dried.

According to a second aspect of the present invention there are calcium phosphate nanoclusters wherein each nanocluster comprises calcium, phosphate and multiply phosphorylated phosphopeptide molecules, provided that no more than 80% of the phosphopeptide molecules are β-casein 4P (f1-25) and provided also that no more than 80% of the phosphopeptide molecules are β-casein 5P (f1-42).

A calcium phosphate nanocluster formed from a solution containing the β-casein phosphopeptide residues 1-25 has the empirical formula $$[Ca_{8.47}(HPO_4^{2-})_{1.95}(PO_4^{3-})_{4.55}(H_2O)_{14.7}]$$
$$[Ca_{4.7}SerP_4\text{-Casein}]$$

wherein SerP$_4$-Casein is the phosphopeptide. These particles are thermodynamically stable in the pH range 6.0-7.2 and have a solubility product, $K_s$, given by $$K_s\{Ca^{2+}\}^{1.0}\{HPO_4^{2-}\}^{0.3}\{PO_4^{3-}\}^{0.467}$$

$$K_s = 8.671(\pm 0.600).10^{-9} M^{1.767}$$

Preferably, the nanoclusters have an empirical formula in the range $[Ca(HPO_4^{2-})_{0.04-1.0}(PO_4^{3-})_{0-0.3}(H_2O)_x]_{5-15}$ $[Ca_{2-5}SerP_y\text{-peptide}]$ where $(y \geq 3)$ and the sum of charges of the ions within both square brackets is approximately zero and where $Ca_{2-5}SerP_y$-peptide is the calcium salt of a multiply phosphorylated phosphopeptide molecule.

Preferably, a phosphopeptide molecule has a centre of phosphorylation.

Preferably, a centre of phosphorylation has at least 3 phosphorylated residues.

More preferably, a centre of phosphorylation has at least 3 phosphorylated residues close together in the multiply phosphorylated peptide.

Most preferably, a centre of phosphorylation has at least 3 phosphorylated residues in a series of 6 consecutive residues in the primary structure of the phosphopeptide molecule.

Preferably, a phosphopeptide molecule contains few or no hydrophobic regions.

Preferably also, a phosphopeptide molecule contains only one centre of phosphorylation.

A nanocluster may have a plurality of different types of phosphopeptide molecule.

A plurality of different types of phosphopeptide molecule may be selected from phosphopeptide molecules derived from an enzymatic digest of a crude casein preparation.

Typically, the nanocluster will comprise 10-200 of the approximate empirical formula units.

Preferably, the nanocluster does not have significant amounts of magnesium therein.

Preferably also, the nanocluster does not have significant amounts of citrate therein.

A dispersing agent may be included.

A preservative may also be included.

The nanoclusters may be sterilized.

According to a third aspect of the present invention there are provided nanoclusters obtainable by the method of first aspect.

According to a fourth aspect of the present invention there is provided a calcium containing food or beverage comprising nanoclusters according to the second or third aspect.

According to a fifth aspect of the present invention there is provided a pharmaceutical composition for the inhibition or prevention of tooth demineralisation, the composition comprising nanoclusters according to the second or third aspect.

According to a sixth aspect of the present invention, there is provided a pharmaceutical composition for the treatment or prevention of pathological calcification, the composition comprising phosphopeptides according to the second or third aspect and a pharmaceutically acceptable carrier.

According to a seventh aspect of the present invention there is provided a pharmaceutical, composition for a soluble mixture of essential trace elements.

The pharmaceutically acceptable carrier may comprise an ion permeable matrix.

Preferably, the ion permeable matrix is a gel.

The ion permeable matrix may be a casein based gel.

The present invention will now be described with reference to the following Figures in which:

FIGS. 1a and 1b show reversed phase high pressure liquid chromatograms following a modification of the procedure of Ellegard et al. (1999) of (1a) the retentate and ultrafiltrate of a calcium phosphate nanocluster solution, prepared by a method similar to A4 and (1b) an optimised subtraction of the ultrafiltrate from the retentate.

Examples of a method for making calcium phosphate nanoclusters are described in depth below. In general, the method consists of a defined sequence of operations involving first the dissolution of the phosphopeptide powder in a volume of water, followed by the addition of known volumes of stock solutions of salts, including phosphate salts (e.g. sodium dihydrogen phosphate and/or disodium hydrogen phosphate and or trisodium phosphate), and, depending on the final pH to be attained, a volume may be added of either an acid or an alkali. It is preferred that, in the final stage, a volume of a stock solution of a calcium salt is added with stirring to achieve the final composition and pH.

The order in which the stock solutions are added can varied so that the final stage could be either a final adjustment of pH with an alkali or a final addition of the calcium solution or one of the phosphate salts but in all cases it is preferred that the addition is made slowly and with stirring to minimise the turbidity of the solution. In the presence of sufficient phosphopeptide, larger nanoclusters formed during mixing will decrease in size slowly to an equilibrium value, and even precipitated calcium phosphate will spontaneously redisperse.

The new method of making nanoclusters differs from the previously published method in three essential respects. First it uses different phosphopeptides or phosphoproteins or a mixture of phosphopeptides rather than a single peptide. Second, it uses a different procedure for achieving the final pH which was only considered possible after further undisclosed research had been completed. The method differs in a third, respect in that neither magnesium nor citrate salts were found to be needed and were eliminated for normal purposes.

This method has been developed from never previously disclosed research which contradicts the current theory of nanocluster formation. We have shown that the nanoclusters are not kinetically stabilized but in fact have thermodynamic stability. In a first experiment, a nanocluster solution was taken to pH>8 where it precipitated, as thought, into a more thermodynamically stable state. However, when the suspension of the precipitate was readjusted to neutral pH, the precipitate spontaneously reformed the nanoclusters. In a second, even more convincing, experiment, phosphopeptide was added to a fresh calcium phosphate precipitate wherein the precipitate was seen to disappear slowly even though the condition of supersaturation was not changed. In other words, the nanoclusters are more thermodynamically stable than the precipitated phase. There is no known precedent for this result.

These experiments lead to a new theory which states that the nanoclusters are thermodynamically stable entities and we need not be so concerned about the kinetic, non-equilibrium aspects of their formation since they will achieve the core-shell nanocluster structure on standing even if there is some initial precipitation. We therefore experimented with simple mixing procedures that gave a minimum amount of precipitation and found that they worked. The surprising discovery that simple mixing can be used to form nanoclusters, in flat contravention of the currently accepted theory, is of great benefit in that it reduces the complexity of the manufacturing process.

The method herein disclosed preferably uses a phosphopeptide mixture. Again, currently accepted theory described above indicates that if a mixture of phosphopeptides were used, some would be capable of bridging between two nanocluster particles, giving a network or gel. Given accepted theory at the present time, it is therefore surprising that a mixture may be used. It is much easier to manufacture a phosphopeptide mixture than it is to manufacture a pure phosphopeptide.

Furthermore, the method disclosed herein eliminates magnesium and citrate. As discussed above, magnesium and citrate were though to help the more powerful phosphopeptide to form important stable intermediate nanoclusters as part of the nanocluster formation process. As magnesium and citrate are known inhibitors of the rate of precipitation, the surprising discovery that they may be removed is of great benefit.

With all these changes in method of preparation in comparison with the prior Art and in contravention of previously accepted theory, nanocluster-like particles are still formed but they can have a different composition, namely that different phosphopeptides are present in the shell. As a general rule, only phosphopeptides containing three or more phosphorylated residues within a short sequence of the primary structure are capable of forming (part of) the shell and in a casein phosphopeptide mixture, all peptides satisfying this criterion are bound in the nanoclusters to some degree.

The resulting calcium phosphate nanoclusters are particles having a core-shell structure with the core comprising largely a salt of calcium phosphate with a radius of a few nanometers and a shell composed largely of a phosphopeptide or a mixture of phosphopeptides or a phosphoprotein or a mixture of phosphoproteins.

Other components that are not essential to the formation of the nanocluster can become incorporated, either by design or accident. For example, magnesium ions and citrate ions can become bound to the nanoclusters if present in the solution. If β-casein is used as the phosphoprotein then a dispersing agent such as κ-casein can be used to prevent or reduce adherence of the nanoclusters to form larger macroclusters or colloidal aggregates.

Calcium phosphate nanoclusters can form and be stable at about neutral pH but can form a gelatinous phase at pH 8 or greater. Manoclusters can form if the solution is saturated with respect to calcium phosphate, as defined by a solubility product relationship which takes the approximate form in milk of:

$$K_s = \{Ca^{2+}\}\{PO_4^{3-}\}^{0.2}\{HPO_4^{2-}\}^{0.7};$$
$$1.6 \cdot 10^{-7} \leq K_s \leq 10^{-6} M^{1.9}.$$  (Equation 1)

Where $K_s$ is a constant for a given type of nanocluster, $\{Ca^{2+}\}$ is the activity of calcium ions, $\{PO_4^{3-}\}$ is the activity of the phosphate trianion and $\{HPO_4^{2-}\}$ is the activity of the phosphate dianion.

The Calcium phosphate nanoclusters produced have an approximate empirical formula:

$$[Ca_{8.47}(HPO_4^{2-})_{1.95}(PO_4^{3-})_{4.55}(H_2O)_{14.7}]$$
$$[Ca_{4.7}SerP_4\text{-Casein}]$$

where $Ca_{4.7}SerP_4$-peptide is a calcium salt of a phosphopeptide containing preferably at least three and usually four phosphorylated residues close together in the primary structure. However, the composition can vary depending on the rate of pH change in the final stage of formation, the composition of the salt solution and the amount and nature of the phosphopeptide.

The range of possible concentrations is thought to be:

$$[Ca(HPO_4^{2-})_{0.4-1.0}(PO_4^{3-})_{0-0.3}(H_2O)_x]_{5-15}.$$
$$[Ca_{2-4}SerP_y\text{-peptide}]$$  (Equation 2a)

where ($y \geq 3$) and the sum of charges within both square brackets is approximately zero.

An actual nanocluster will comprise some, usually small, number of multiples of the empirical formula, for example 49±4 in the standard nanocluster preparation of Holt et al. (1998).

Notwithstanding the above, the constraints on the composition of a solution able to form stable calcium phosphate nanoclusters can be represented by the following approximate empirical relations which apply to a commercial phosphopeptide preparation (PP) derived from a tryptic digest of whole casein in a solution of calcium and phosphate salts but containing no more than minor amounts of other strong calcium chelating agents such as citrate.

$$[Ca]/[PP] \geq 1.5.$$  (Equation 3)

$$[P_{i,t}] = (0.875 \pm 0.125) \cdot [PP] - 1.67 \pm 0.25$$  (Equation 4)

where [PP] is the concentration of the phosphopeptide in grams per litre, $[P_{i,t}]$ is the total millimolar concentration of inorganic phosphate and $[Ca_t]$ is the total millimolar calcium concentration.

A range of phosphopeptides may be used, as indicated in the following investigation:

Nanocluster formation was investigated with the following phosphoproteins, phosphoprotein mixtures, phosphopeptides and phosphopeptide mixtures:
1. Whole casein
2. Mixtures of β- and κ-caseins
3. β-casein 5P
4. A commercial phosphopeptide mixture supplied by MD foods and derived from casein, containing a large number of phosphopeptides as described by Ellegård et al. (1999).
5. A phosphopeptide mixture derived from a digestion of whole casein with protease XIV from *Streptomyces griseus*, and papain type IV containing $\alpha_{s1}$-casein 2P (f46-51), $\alpha_{s1}$-casein 4P (f61-70), β-casein 4P (f11-21), $\alpha_{s2}$-casein 3P (f5-12), $\alpha_{s2}$-casein 4P (f49-61) and $\alpha_{s2}$-casein 2P (f126-133).
6. β-casein phosphopeptides 4P (f1-25) or 4P (f2-25) or 5P (f1-42)
7. Cyanogen bromide cleavage fragments $\alpha_{s1}$-casein 2P (f1-54) or $\alpha_{s1}$-casein 6P (f61-123).
1. Tryptic phosphopeptides $\alpha_{s1}$-casein 1P (f104-119) or $\alpha_{s1}$-casein 2P (f43-58) or $\alpha_{s1}$-casein 5P (f59-79) or $\alpha_{s1}$-casein 7P (f43-79)

A test for nanocluster formation was applied in which the standard conditions for the formation of nanoclusters from the β-casein phosphopeptide were modified to the smallest extent possible and applied to the other peptides or peptide mixtures. Absence of precipitation was evidence of the formation of nanocluster-like particles. Conditions were found with the phosphopeptide mixes 4 and 5 and the phosphoproteins 1 and 2 where a stable clear solution was formed but 3 underwent an unlimited aggregation. With 4, HPLC showed that the less phosphorylated peptides were concentrated in the serum rather than being on the nanoclusters. Formation of nanocluster-like particles by 4 was confirmed experimentally by X-ray scattering measurements. Nanoclusters were found with each of the 6 phosphopeptides and confirmed experimentally by X-ray scattering measurements. The cyanogen bromide peptides of 7 either failed to dissolve ($\alpha_{s1}$-casein 2P (f1-54)) or formed a precipitate in the test system ($\alpha_{s1}$-casein 6P (f61-123). Nanoclusters were formed with either the 5P or 7P fractions of 8 and confirmed experimentally by X-ray scattering measurements. No stable nanocluster solution was formed with either the 1P or 2P peptide in 8.

In conclusion, peptides or proteins containing 3 or more phosphorylated residues in a short sequence of the primary structure are able to form calcium phosphate nanocluster-like particles under favourable conditions. A typical centre of phosphorylation in casein would have 4 phosphorylated residues in the space of 5 or 6 amino acids.

Peptides should contain few if any hydrophobic regions to avoid the use of another dispersing agent but such an agent can be used as needed. The peptides should preferably contain only one centre of phosphorylation to avoid cross linking although a small amount of such a peptide in mixtures with other suitable peptides does not cause serious problems. The peptide should preferably be readily soluble. This new research indicates the general principle which can be used to find other useful phosphopeptides; for example, digests of $\alpha_{s1}$-casein, phosvitin and $\alpha_{s2}$-casein.

Equations 1 and 2 together define within fairly close limits the extent of formation of nanocluster particles in solutions of calcium and phosphate salts, a background electrolyte and a suitable phosphoprotein or phosphopeptide. Significant modifications of the composition of the solution by the inclusion for example of other, normally multivalent, anions or cations, requires a modification to equations 1 and 2 to make account of the strong interactions.

The upper limit of calcium concentration possible using the calcium phosphate nanocluster system within the scope of the present invention is not known. However, initial experimentation has managed to prepare solutions up to 30 times more concentrated than cow's milk. It should be possible to provide very high concentrations of Calcium, e.g. 1M compared to 0.008M in human milk. This allows the preparation of nutraceutical drinks, foodstuffs or additives for food and drink which allow a consumer to gain a high calcium intake from only a small volume of produce.

EXAMPLE METHOD

The example method uses a commercial phosphopeptide mixture from MD Foods (NaCPP) described by K. H. Ellegård, C. Gammelgård-Larsen, E. S. Søorensen & S. Fedosov. Process scale chromatographic isolation, characterization and identification of tryptic bioactive casein phosphopeptides, International Dairy Journal 9 639-652 (1999).

The sample was prepared using the following stock solutions made up to the indicated molar concentration with deionised water:

TABLE 1

Stock solutions used to form calcium phosphate nanoclusters

| Substance | Concentration (M) |
|---|---|
| $CaCl_2$ | 0.200 |
| NaCl | 1.000 |
| $NaH_2PO_4$ | 0.200 |
| $Na_2HPO_4$ | 0.200 |
| $Na_3PO_4$ | 0.200 |
| NaOH | 1.000 |
| $NaN_3$ (1%) | 0.154 |

The sodium azide addition is for inhibition of bacterial growth and may be omitted or replaced by filter or steam sterilization, as appropriate to the end use. Sodium chloride is not important in nanocluster formation and is present primarily to give a particular application related ionic strength, for example, to give a solution with an ionic strength approximately that of baby milk. Potassium salts may be used in place of the sodium salts provided the solubility is great enough and the chloride salts can be replaced by nitrates or any other equally soluble salt.

The peptide is dissolved in a certain volume of water calculated as the final volume less the sum of the volumes of each of the stock solutions required to give the final composition and less a volume contribution from the peptide which is calculated from an assumed partial specific volume of 0.7 ml $g^{-1}$.

Method A1 Preparation of 3 ml of Solution Containing 30 mM Ca

To 60 mg of the phosphopeptide powder, add 2.145 ml deionised water with stirring until dissolved. Place a calibrated glass pH electrode in the solution and stir, using a magnetic follower at about 60 rpm while measuring the pH after every addition of one of the above stock solutions. All the additions are made over a period of about 30 min. With the objective of obtaining a final pH of 6.7±0.05 but without ever allowing the solution to become more alkaline than 6.75, the order of addition is as follows:

TABLE 2

Example sequence of additions

| Stock Solution | Addition (µl) | Cumulative Volume (ml) | pH |
|---|---|---|---|
| $CaCl_2$ | 450 | 2.595 | 6.91 |
| NaCl | 150 | 2.745 | 6.942 |
| $NaN_3$ | 30 | 2.775 | 6.995 |
| $NaH_2PO_4$ | 20 | 2.795 | 6.764 |

TABLE 2-continued

Example sequence of additions

| Stock Solution | Addition (µl) | Cumulative Volume (ml) | pH |
|---|---|---|---|
| $Na_3HPO_4$ | 30 | 2.825 | 6.704 |
| $NaH_2PO_4$ | 10 | 2.835 | 6.653 |
| $Na_2HPO_4$ | 40 | 2.875 | 6.675 |
| $Na_2HPO_4$ | 60 | 2.935 | 6.719 |
| $NaH_2PO_4$ | 10 | 2.945 | 6.671 |
| $Na_2HPO_4$ | 30 | 2.975 | 6.703 |
| $NaH_3PO_4$ | 10 | 2.985 | 6.665 |
| $Na_2HPO_4$ | 15 | 3.000 | 6.686 |

The final composition of the sample was as follows:

TABLE 3

Final composition of the nanocluster solution

| Substance | Concentration, mM |
|---|---|
| Ca | 30 |
| Total inorganic P | 15 |
| Na | 76.66 |
| Cl | 110 |
| Total organic P[1] | 19.61 |
| Total peptide[2] | 8.94 |

[1] 3.03% w/w Total P in the NaCPP
[2] Mean peptide mass 2.237 Da

Method A2 Preparation of 3 ml of Solution Containing 30 mM Ca

Add all the ingredients as single additions of the stock solutions after first dissolving the phosphopeptide powder in the water. All additions are made slowly by micropipette with the pipette tip submerged. Although the pH becomes more alkaline than the target final pH, this occurs in the absence of calcium and the addition of the calcium chloride brings the pH down so turbidity does not develop.

TABLE 4

Example additions to form the nanocluster solution

| Stock Solution | Addition (µl) | Cumulative Volume (ml) | pH |
|---|---|---|---|
| $H_2O$ | 2103 | 2.145 | — |
| $NaN_3$ | 30 | 2.175 | — |
| NaCl | 150 | 2.325 | — |
| $NaH_2PO_4$ | 50 | 2.375 | 7.239 |
| $Na_2HPO_4$ | 175 | 2.550 | 7.471 |
| $CaCl_2$ | 450 | 3.000 | 6.710 |

Method A2 is preferred over method A1 because it is simpler to perform.

Method A3 Preparation of 100 ml of Solution Containing 90 mM Ca

This is an adaptation of method A2. Dissolve 6 grams of the NaCPP commercial phosphopeptide in 20 ml deionised water. Additions are made in the following order except for the two phosphate solutions, which are premixed in the right ratio so that only a single addition is needed. Each addition is made slowly by micropipette with stirring over a period of about 30 min.

TABLE 5

Example additions to form the nanocluster solution

| Stock Solution | Addition (ml) | Cumulative Volume (ml) | pH |
|---|---|---|---|
| $H_2O$ | 20 | 24 | — |
| $NaN_3$ | 1 | 25 | — |
| NaCl | 5 | 30 | — |
| $NaH_2PO_4$ | 12 | 42 | — |
| $Na_3PO_4$ | 13 | 55 | — |
| $CaCl_2$ | 45 | 100 | 6.76 |

Method A4 Preparation of 4.5 ml of Solution Containing Approximately 1-M Ca

This was achieved by ultrafiltration of 50 ml of the solution prepared by method A3 through a Diaflo ultrafiltration membrane type XM50 in a 10 ml stirred cell (Amicon Ltd, Stonehouse, Glos.) at a pressure of 15 pounds per square inch until the final volume was approximately 4.5 ml. The retentate retains the nanocluster particles while allowing the uncompleted peptides and salts to permeate the membrane.

Method A5 Preparation of Very High Calcium Concentration Solutions from Freeze Dried Nanoclusters Freeze dry 10 ml of the solution prepared by method A3 and reconstitute in a suitable volume of water to achieve the desired concentration, for example 0.9 ml to give an approximately 1-M solution. By isolating freeze-dried nanoclusters and reconstituting them in this way, very high concentrations of calcium can be obtained.

Methods A4 and A5 are the best method for preparing concentrations above about 200 mM calcium. Method A5 is expected to be cheapest and to have the potential for the highest calcium concentrations.

Method A6 Preparation of a Solution of Essential Trace Elements

The formulation contains recommended adult allowances of Ca, Mg, Fe, Cn, Mn, I and Zn in a volume of 300 ml.

To prepare 100 ml of the solution, dissolve 6 g of the NaCPP commercial phosphopeptide mixture in distilled water to a final volume of 52.2 ml. Add stock solutions in the following sequence, with stirring.

| Salt | Concentration (mM) | Volume (ml) | Final Concentration |
|---|---|---|---|
| $NaH_2PO_4 \cdot H_2O$ | 200 | 10 | 60 mM Phosphate |
| $Na_3PO_4$ | 200 | 20 | 60 mM Phosphate |
| $FeCl_3 \cdot 6H_2O$ | 100 | 1.0 | 1.0 mM Fe |
| $ZnCl_2$ | 100 | 0.6 | 0.6 mM Zn |
| $CuSO_4 \cdot 5H_2O$ | 10 | 0.8 | 80 µM Cu |
| $MnSO_4 \cdot H_2O$ | 10 | 2.0 | 200 µM Mn |
| KI | 1 | 0.4 | 4 µMI |
| $MgCl_2 \cdot 6H_2O$ | 1000 | 4.0 | 40 mM Mg |
| $CaCl_2 \cdot 2H_2O$ | 1000 | 9.0 | 90 mM Ca |

The solution becomes turbid after the addition of the magnesium and calcium solutions but gradually clears on leaving for 2 days, with stirring.

Freeze drying produced 7.59 g of powder.

The freeze dried powder redissolves readily in water to form a nearly clear solution with a pH of 7.1. One gram of the freeze dried powder containing 0.74 mg Fe, which can therefore be used in a readily soluble form.

Properties of the Sample

A calcium phosphate nanocluster solution prepared by a method similar to A4 was analysed for phosphopeptides in the retentate and in the ultrafiltrate by reversed phase high pressure liquid chromatography following a modification of the procedure of Ellegård et al. (1999).

Peptides were separated on a C18 reversed phase Apex Wide-pore column (ex Jones Chromatography Ltd.) Column dimensions were 25 cm×4.4 mm internal diameter. An acetonitrile gradient of 5 to 35% over 30 min was used at a flow rate or 1 ml/min and a temperature of 46 degrees C. Trifluoroacetic acid (0.1% v/v) was present in the eluting buffers. Detection was at 214 nm.

FIG. 1 shows the resulting chromatograms. FIG. 1a shows the chromatograms for the retentate and ultrafiltrate. FIG. 1b shows an optimised subtraction of the ultrafiltrate from the retentate to reveal the profile of the fractions bounds to the nanoclusters.

The ultrafiltrate chromatogram is closely comparable to that of Ellegård et al. (1999) and shows a wide range of different phosphopeptides. The chromatogram or the retentate is somewhat different and shows the differential binding of phosphopeptides to the nanocluster particles since only the latter are fully retained during ultrafiltration. Thus it may reasonably be concluded that the nanocluster particles made with the NaCPP are stabilised by a broad mixture of phosphopeptides.

The formation of nanoclusters, nanocluster-like particles or larger particles composed of assemblies of nanoclusters has been established by small angle X-ray or neutron scattering experiments, as described by Holt et al. (1996, 1998).

TABLE 6

Confirmation of nanocluster formation by small angle X-ray or neutron scattering

| Sample | Conclusion |
|---|---|
| Whole casein | Milky solution containing particles of the size and substructure of native casein micelles. |
| Mixtures of β- and κ-caseins | Turbid or milky solutions depending on the ratio of κ- to β-caseins. Size was inversely proportional to the ratio from a minimum radius of gyration of 11 nm. |

TABLE 6-continued

Confirmation of nanocluster formation by small angle X-ray or neutron scattering

| Sample | Conclusion |
|---|---|
| | At small ratios a substructure is seen closely similar to that of native casein micelles |
| β-casein 5p | Uncontrolled precipitation of the β-casein aggregates showing the need for an additional dispersing agent. |
| A commercial phosphopeptide mixture (NaCPP) supplied by MD foods. | Clear, stable solutions of nanocluster-like particles could be formed but the particles were polydisperse with a size range extending from several nanometers to several tens of nanometers |
| A phosphopeptide mixture derived from a digestion of whole casein with protease XIV from *Streptomyces griseus*, and papain type IV containing $\alpha_{s1}$-casein 2P (f46-51), $\alpha_{s1}$-casein 4P (f61-70), β-casein 4P (f11-21), $\alpha_{s2}$-casein 3P (f5-12), $\alpha_{s2}$-casein 4P (f49-61) and $\alpha_{s2}$-casein 2P (f126-133). | Clear, stable solutions of nanocluster-like particles could be formed but the particles were polydisperse with a size range extending from several nanometers to several tens of nanometers |
| β-casein phosphopeptide 4P (f1-25) | Monodisperse nanoclusters formed (Holt et al., 1996, 1998) |
| β-casein phosphopeptide 4P (f2-25) | Monodisperse nanoclusters formed |
| β-casein phosphopeptide 5P (f1-42) | Monodisperse nanoclusters formed (Holt et al., 1996, 1998) |
| Cyanogen bromide cleavage fragment $\alpha_{s1}$-casein 2P (f1-54) | Peptide aggregation during the preparation of the sample |
| Cyanogen bromide cleavage fragment $\alpha_{s1}$-casein 6P (f61-123). | Peptide aggregation during the preparation of the sample |
| Tryptic phosphopeptide $\alpha_{s1}$-casein 1P (f104-119) | Precipitation of calcium phosphate |
| Tryptic phosphopeptide $\alpha_{s1}$-casein 2P (f43-58) | Precipitation of calcium phosphate |
| Tryptic phosphopeptide $\alpha_{s1}$-casein 5P (f59-79) | Clear solution of stable nanoclusters in the normal size range |
| Tryptic phosphopeptide $\alpha_{s1}$-casein 7P (f43-79) | Clear solution of stable nanoclusters in the normal size range |

Further modifications and alterations may be made within the scope of the invention herein described.

The invention claimed is:

1. Thermodynamically stable calcium phosphate nanoclusters formed from a nanocluster forming solution comprising calcium, phosphate and either casein-type peptides or casein-type peptide mixtures, with a ratio of 10:4.9:3.0, for Ca:$P_i$:$P_o$ where $P_i$ and $P_o$ are the inorganic and organic phosphorus respectively.

2. Thermodynamically stable calcium phosphate nanoclusters as claimed in claim 1, containing beta casein phosphopeptide residues 1 to 25, and having the empirical formula:

$$[Ca_{8.47}(HPO_4^{2-})_{1.95}(PO_4^{3-})_{4.55}(H_2O)_{14.7}]$$
$$[Ca_{4.7}SerP_4\text{-Casein}]$$

where $SerP_4$-Casein is the phosphopeptide.

3. Thermodynamically stable calcium phosphate nanoclusters as claimed in claim 1, wherein the particles are thermodynamically stable in the pH range 6.0 to 7.2 and have a solubility product, $K_s$ such as:

$$K_s = \{Ca^{2+}\}\{PO_4^{3-}\}^{0.2}\{HPO_4^{2-}\}^{0.7};$$
$$1.6 \cdot 10^{-7} \leq K_s \leq 10^{-6} \, M^{-1.9}$$

or $$K_s = \{Ca^{2+}\}^{1.0}\{HPO_4^{2-}\}^{0.3}\{\{PO_4^{3-}\}^{0.467}$$

or $$K_s = 8.671(\pm 0.6000) \cdot 10^{-9} \, M^{1.767}.$$

4. Thermodynamically stable calcium phosphate nanoclusters as claimed in claim 1, wherein the nanoclusters have an empirical formula in the range:

$$[Ca(HPO_4^{2-})_{0.4-1.0}(PO_4^{3-})_{0-0.3}(H_2O)_x]_{5-15}.$$
$$[Ca_{2-5}SerP_y\text{-peptide}]$$

$$[Ca(HPO_4^{2-})_{0.4-1.0}(PO_4^{3-})_{0-0.3}(H_2O)_x][Ca_{2-5}SerP_y\text{-peptide}]$$

where ($y \geq 3$) and the sum of charges of the ions within both square brackets is approximately zero and where $Ca_{2-5}SerP_y$-peptide is the calcium salt of a casein-type peptide or casein-type peptide mixture.

5. Thermodynamically stable calcium phosphate nanoclusters as claimed in claim 1, wherein a plurality of different types of casein-type peptides or casein-type peptide mixtures may be selected from casein-type peptides or casein-type peptide mixtures derived from an enzymatic digest of whole casein preparation.

6. Thermodynamically stable calcium phosphate nanoclusters as claimed in claim 1, wherein the nanoclusters comprise 10 to 200 of the approximate empirical formula units.

7. Thermodynamically stable calcium phosphate nanoclusters as claimed in claim 1, wherein the casein-type peptide has a center of phosphorylation.

8. Thermodynamically stable calcium phosphate nanoclusters as claimed in claim 7, wherein the center of phosphorylation has at least three phosphorylated residues.

9. Thermodynamically stable calcium phosphate nanoclusters as claimed in claim 7, wherein the center of phosphorylation has at least three phosphorylated residues close together in the multiple phosphorylated casein-type peptide.

10. Thermodynamically stable calcium phosphate nanoclusters as claimed in claim 7, wherein the center of phosphorylation has at least three phosphorylated residues in a series of six consecutive residues in the primary structure of the casein-type peptide.

11. Thermodynamically stable calcium phosphate nanoclusters as claimed in claim 1, wherein the casein-type peptide contains two centers of phosphorylation.

12. Thermodynamically stable calcium phosphate nanoclusters as claimed in claim 1, wherein the casein-type peptide contains three or more centers of phosphorylation.

13. A calcium containing food or beverage comprising thermodynamically stable calcium phosphate nanoclusters as claimed in claim 1.

14. A pharmaceutical composition for the inhibition of tooth demineralisation, comprising thermodynamically stable calcium phosphate nanoclusters as claimed in claim 1.

15. A pharmaceutical composition for the treatment of pathological calcification, the composition comprising thermodynamically stable calcium phosphopeptide nanoclusters as claimed in claim 1, and a pharmaceutically acceptable carrier.

16. A pharmaceutical composition for the treatment of pathological calcification as claimed in claim 15, wherein the pharmaceutically acceptable carrier comprises an ion permeable matrix.

17. A pharmaceutical composition for the treatment of pathological calcification as claimed in claim 16, where the ion permeable matrix is a gel.

18. A pharmaceutical composition for the treatment of pathological calcification as claimed in claim 17, wherein the ion permeable matrix is a casein based gel.

19. A pharmaceutical composition for a soluble mixture of essential trace elements comprising thermodynamically stable calcium phosphate nanoclusters as claimed in claim 1, and essential trace elements.

20. A pharmaceutical composition for a soluble mixture of essential trace elements as claimed in claim 19, wherein the essential trace elements may be one or more from the list of calcium, magnesium, iron, manganese, iodine and zinc.

21. Thermodynamically stable calcium phosphate nanoclusters, wherein the nanoclusters have an empirical formula in the range:

$$[Ca(HPO_4^{2-})_{0.4-1.0}(PO_4^{3-})_{0-0.3}(H_2O)_x]_{5-15}.$$
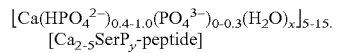

where ($y \geq 3$) and the sum of charges of the ions within both square brackets is approximately zero and where $Ca_{2-5}SerP_y$-peptide is the calcium salt of a casein-type peptide or casein-type peptide mixtures.

* * * * *